United States Patent [19]

Enloe

[11] Patent Number: 4,704,116
[45] Date of Patent: Nov. 3, 1987

[54] DIAPERS WITH ELASTICIZED SIDE POCKETS

[75] Inventor: Kenneth M. Enloe, Neenah, Wis.

[73] Assignee: Kimberly-Clark Corporation, Neenah, Wis.

[21] Appl. No.: 786,891

[22] Filed: Oct. 11, 1985

Related U.S. Application Data

[63] Continuation-in-part of Ser. No. 627,164, Jul. 2, 1984, abandoned.

[51] Int. Cl.[4] .............................................. A61F 13/16
[52] U.S. Cl. ................................ 604/385 A; 604/390; 604/358
[58] Field of Search ...................... 604/385.2, 378, 390, 604/358

[56] References Cited

U.S. PATENT DOCUMENTS

| | | | |
|---|---|---|---|
| 3,860,003 | 1/1975 | Buell | 604/385.1 |
| 4,040,423 | 8/1977 | Jones, Sr. | 604/378 |
| 4,490,148 | 12/1984 | Beckestrom | 604/385.1 |
| 4,496,360 | 1/1985 | Joffe et al. | 604/397 |
| 4,500,316 | 2/1985 | Damico | 604/389 |

Primary Examiner—C. Fred Rosenbaum
Assistant Examiner—Sherri E. Vinyard
Attorney, Agent, or Firm—John L. Chiatalas

[57] ABSTRACT

A garment with a backsheet (12), a bodyside liner (14) essentially coterminous with the backsheet (12) and forming a shape with a front waist section (18), a back waist section (20) and side sections connecting the front waist section (18) to the back waist section (20) and first and second flaps (30, 32) formed from or attached to bodyside liner (14). Flaps (30, 32) may have elastic members (40, 42) applied thereto respectively. Flaps (30, 32) may be folded inwardly and respective ends thereof may be bonded to bodyside liner (14) so that edges of flaps are directed toward a centerline (38) of the garment. The flaps (30, 32) may be attached to or formed from bodyside liner (14) along lines (34, 36) which are parallel to centerline (38) or which diverge from or converge toward centerline (38). Additionally, flaps (30, 38) may have varying width and be less than full length.

67 Claims, 8 Drawing Figures

DIAPERS WITH ELASTICIZED SIDE POCKETS

CROSS REFERENCE TO RELATED APPLICATIONS

This application is a continuation-in-part of copending U.S. patent application, Ser. No. 627,164, filed July 2, 1984 now abandoned.

TECHNICAL FIELD

The present invention relates, generally, to the field of disposable garments utilized for the absorption and containment of urine and other body exudates. More particularly, the present invention relates to disposable garments with a provision for the containment of urine and liquid fecal material. Most particularly, the present invention relates to disposable garments that provide enhanced containment of urine and liquid fecal material with elasticized side pockets or flaps formed from or attached to a bodyside liner of the disposable garment.

BACKGROUND ART

Disposable garments are generally well known in the art and have become an important and essentially indispensable sanitary protection item, most particularly in the field of infant and child care where disposable diapers provide for the absorption and containment of urine and other body exudates. Present commercially available disposable diapers are generally unitary, preshaped and prefolded, and comprised of a liquid pervious bodyside liner, a fluid impervious backing sheet with an absorbent material disposed therebetween. These presently available disposable diapers have met a particular need and have become ever increasingly popular. However, even though the presently available disposable diapers are efficient and effective, they have several drawbacks that have been identified by mothers of infants wearing the diapers. Although the presently available diapers have elasticized leg openings which provide a better fit and enhanced containment of fluid exudates, they have not been entirely successful in stopping leakage from explosive liquified bowel movements and rapid discharges of urine.

Another drawback associated with presently commercially available disposable diapers is skin irritation caused by urine, feces or moisture trapped next to the skin. The feces, if remaining next to the skin, can smear causing problems in cleanup.

The attempts to solve these drawbacks associated with the present commercially available disposable diapers have extended over several years and include several different concepts. For example, U.S. Pat. No. 3,999,547 to Hernandez discloses a disposable diaper with a waterproof back sheet, a hydrophobic sheet, and an absorbent pad sandwiched between the back sheet and the face sheet. The diaper is folded to define a box pleated configuration having a central panel, inwardly extending panels and outwardly extending panels with the inner edges of the inwardly extending panels being in abutting relationship. Sealing strips of waterproof material separate from the back sheet are secured on the face sheet. The sealing strips are formed by folding an excess width of the back sheet over the face sheet forming side flap portions, and then cutting the side flap portions free from the back sheet. The sealing strips may be folded inwardly toward the center of the diaper to form fluid catching seals.

A similar concept is disclosed in U.S. Pat. No. 4,210,143 to De Jonckheere which discloses a disposable diaper for a baby with at least one sheet of flexible liquid impermeable material comprising two longitudinal edges intended t define a waist portion and an absorbent pad superimposed on a central region of the liquid impermeable sheet. The diaper is characterized, in that it comprises, respectively in the immediate vicinity of each of the longitudinal edges, on either side of the pad, a flexible longitudinal sheath inside which a flexible longitudinal tie is able to slide and in that each sheath comprises means for gaining access to the corresponding flexible tie in order to enable the latter to be gripped manually and to be tensioned at will in order to reduce the apparent length of the longitudinal edges, to press the latter at will around the baby's legs and to give the disposable diaper the shape of a trough between the legs.

Another concept is shown in U.S. Pat. No. 4,490,148 to Beckestrom which discloses a protector against incontinence comprising an oblong absorbent body which is fixed to a bottom liquid-tight layer extending outside the absorbent body. The lateral edge portions of the layer are folded in over the absorbent body and form side flaps, the distance between the edges thereof being less than the width of the absorbent body at its mid section. The side flaps are fixed at their ends to the bottom layer. An elastic line, arranged at the edge of each side flap, is designed to contract itself and thereby the edges of the side flaps. When the protector is put on, the edges of the side flaps come into elastic sealing contact in the thigh crease of the crotch.

However, these attempts to solve one problem have resulted in the emergence of other problems. For example, the elasticized flaps can cause the waterproof material of the flaps to provide a tight seal at the thigh crease because the tensioned elastic presses the easily deformable flaps into close contact with the skin. The waterproof material of the flaps can then cause urine or moisture and even liquid fece material to collect next to the skin and cause skin irritation.

The present application teaches an improved disposable garment which provides fluid pervious flaps to enhance the containment and absorption of urine and other fluid exudates as well as solid exudates. The flaps, made up of water pervious material, slows the sideways flow of fluidic material and stops essentially all the sideways flow of solid material. Furthermore, the flaps enhance skin dryness by causing at least one extra layer of material to be disposed between the absorbent area of the diaper and the skin of the wearer. This, in addition to having fecal material separated from the skin by at least one layer of flap material, decreases the potential of skin irritation.

DISCLOSURE OF THE INVENTION

It has now been determined in accordance with the present invention that the disposable diaper with side pockets or flaps can be produced that enhances the containment and absorption of urine and other fluid body exudates, such as liquified fecal material. Advantageously, the disposable diaper of the present invention achieves decreased leakage of urine and other fluid body exudates from around the leg areas of the disposable diaper.

The foregoing, and other advantages of the present invention, are realized in a disposable garment with a back sheet, a bodyside liner essentially coterminous with the back sheet forming a shape with a front waist section and a back waist section with two side sections connecting the front waist section to the back waist section and a pair of flaps, attached to or formed from, the bodyside liner. Each respective flap is disposed inwardly of the respective side sections. The flaps may be essentially rectangular in shape with first and second longitudinal sides essentially parallel to a centerline of the garment wherein the centerline lies between the respective side sections. The longitudinal sides are connected by base sides and both the longitudinal sides and the base sides have preselected dimensions. The longitudinal sides may have a length sufficient to extend from the front waist section to the back waist section. The base sides may have a width in the range from about one-half inch to a width sufficient for a longitudinal side of each flap to be essentially coterminous with the centerline of the garment.

Each flap may have at least one elastic member disposed therein. The elastic member may be applied to the flap with a tension sufficient to cause the flap to conform to the wearer's shape. The elastic member may be applied to the longitudinal edge of the flap. Each flap may also have a second elastic member applied. The second elastic member may be applied intermediate the first elastic member and the other longitudinal side of the flap. The second elastic member may be applied with a tension greater than, less than or equal to the tension of the first elastic member wherein the two elastic members cooperate to cause the flaps to conform to the shape of the wearer.

The flaps may be attached to or formed from the bodyside liner along a pair of curved lines disposed symmetrically on each side of a centerline of the garment. The curved lines may diverge from the centerline in a direction away from the center portion of the garment or the curved lines may converge toward the centerline.

In either case the flaps may have a length sufficient to cover only a portion of the length of the garment. In addition, the width of the flaps may vary. The width may be wider at the ends of the flaps and narrower at the center of the flaps or the width of the flaps may be narrower at the ends of the flaps and wider at the center of the flaps.

Other aspects of the present invention in terms of both construction and mode of operation, as well as fuller appreciation for its manufacture and use, will be gained from an examination of the following detailed description of the modes for carrying out the invention, read in conjunction with the figures of the drawing.

MODES FOR CARRYING OUT THE INVENTION

The present invention relates, generally, to disposable garments utilized for the absorption and containment of urine and other body exudates. The present invention relates more specially to disposable garments that are utilized for the absorption and containment of liquids and fluidic body exudates such as fluidic fecal material. Most particularly, the present invention provides at least one pair of flaps, which may be elasticized, to slow the sideways flow of liquids such as urine, and to essentially prevent the sideways flow of fluidic solids, such as fluidic fecal material. Accordingly, the present invention will now be described with reference to certain modes for carrying out the invention within the aforementioned context. Those skilled in the art will realize that such a description is meant to be exemplary only and should not be deemed limitative respecting the scope of the present invention, for example, in terms of its construction.

Figure 1:
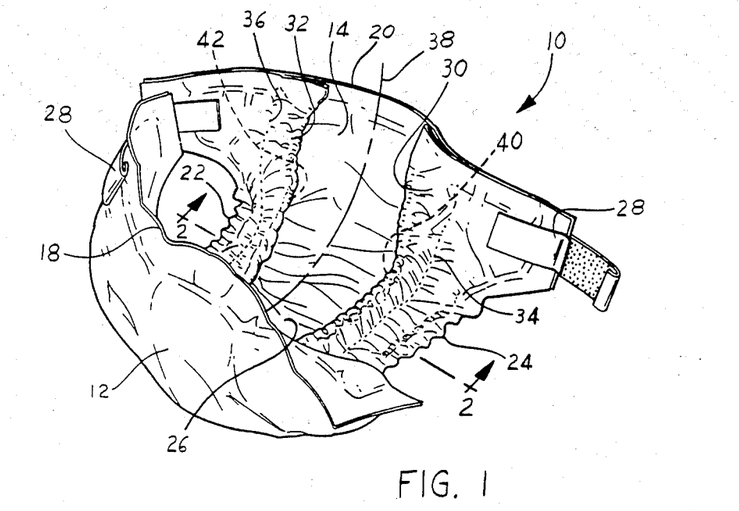
FIG. 1 is a perspective view of the garment of the present invention.
Figure 2:
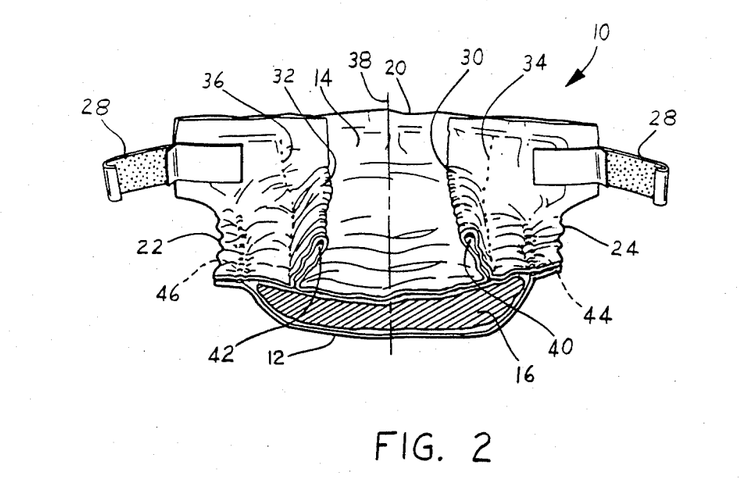
FIG. 2 is a half-perspective view showing a sectional view of cross section 2—2 as shown in FIG. 1.

Turning to the figures, in each of which like parts are identified with like reference characters, FIG. 1 is a perspective view of a disposable garment, in this case, a disposable diaper 10. FIG. 2 is a perspective view of the disposable diaper 10 showing sectional view of cross section 2—2 as shown in FIG. 1. The disposable diaper 10 typically comprises a backsheet 12, a bodyside liner 14 and an absorbent body or pad 16 disposed between backsheet 12 and bodyside liner 14. The bodyside liner 14 is made from a liquid pervious material and backsheet 12 is made from a liquid impervious material. The bodyside liner 14 and backsheet 16 are essentially coterminous and form a shape with a back waist section 20, a front waist section 18 and two side sections, indicated by numerals 22, 24. Intermediate the front waist section 18 and back waist section 20 is a crotch section, indicated by numeral 26. The garment is typically placed around a wearer, such as an infant, and held in place with fastening means, such as tapes shown at 28. Other fastening means can be used without departing from the scope of the present invention. A pair of flaps 30, 32 are attached to or formed from bodyside liner 14 along lines 34, 36 respectively. In either case the crease formed along lines 34, 36 may be "sealed" i.e., by a continuous sonic bond or by a strip of adhesive. The sealing of the crease increases the ability of the structure to maintain its shape and increases the resistance to leakage. Alternatively, the crease can consist of a series of spotbonds. The flaps 30, 32 are attached to, or formed from bodyside liner 14, inwardly of sides 24, 22 respectively. As can be appreciated, if flaps 30, 32 are formed from bodyside liner 14, the flaps are the same material as bodyside liner 14. However, if the flaps are attached to bodyside liner 14, the flaps 30, 32 may be made from a different material. The preferred material for flaps 30, 32 is a liquid pervious material. The flaps 30,32 may be folded inwardly toward a centerline 38 and bonded at each end to the bodyside liner 14. Flaps 30, 32 form pockets into which solid fecal material collects and is contained. Alternately, fluidic fecal material is collected by the pockets and is essentially strained allowing the liquid portion to be absorbed by the absorbent pad or body of the garment. Flaps 30, 32 may have at least one elastic member, indicated at 40, 42, applied thereto. As indicated in FIGS. 1 and 2, the elastic members 40, 42 may be applied essentially at the inwardly directed edge of flaps 30, 32. Also indicated in FIGS. 1 and 2, the disposable garment may additionally have elastic members indicated at 44, 46 in the side portions of the garment, which correspond to the leg sections of the garment. A preferred method of imparting elasticity to the leg sections and the flaps is by extruding a hot melt pressure-sensitive elastomeric adhesive, such as that marketed by H. B. Fuller Company of St. Paul, Minn., U.S.A. under the trademark FULLASTIC. In addition, the elastic members may also comprise any of the usual elastics utilized in the diaper making art such as the utilization of a thin ribbon of natural rubber, etc.

Figure 3:
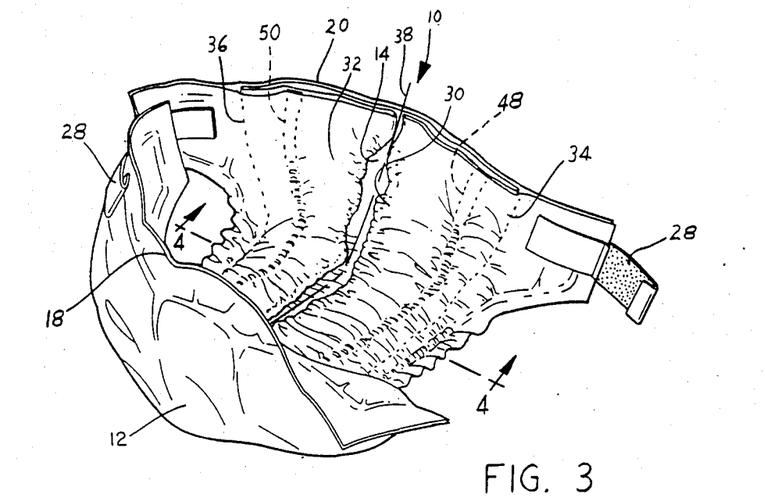
FIG. 3 is a perspective view of an alternative embodiment of the garment of the present invention.
Figure 4:
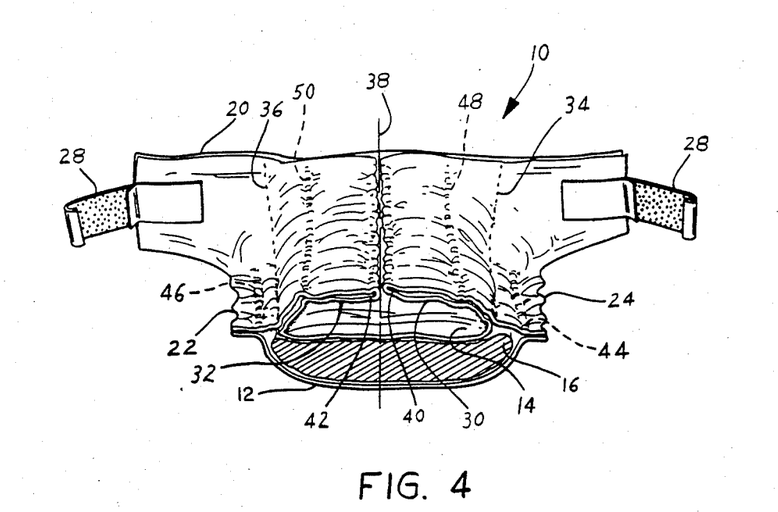
FIG. 4 is a half-perspective view showing a sectional view of cross section 4—4 as shown in FIG. 3.

Referring now to FIGS. 3 and 4, there is shown a perspective view of an alternative embodiment of a garment of the present invention. In this alternative embodiment, flaps 30, 32 have a width sufficient so that inwardly directed edges of the flaps are essentially co-terminous with centerline 38. In addition, flaps 30, 32 may have at least a second elastic member 48, 50 disposed in respective flaps. The second elastic member is applied to the flap intermediate to the first elastic member and the lines 34, 36 respectively. The first elastic member in each flap is applied with a first preselected tension sufficient to cause each flap to conform to the shape of a wearer. The second elastic member in each flap, if applied, is appied with a second preselected tension which may be greater than, less than or equal to the first preselected tension. However, the tensions are selected to cooperate so that the flaps conform to the shape of a wearer. The width of the flaps can be from about one-half inch to a width sufficient for the inwardly directed edge of each flap to be essentially co-terminous with the centerline 38 as shown in FIGS. 3 and 4.

Figure 5:
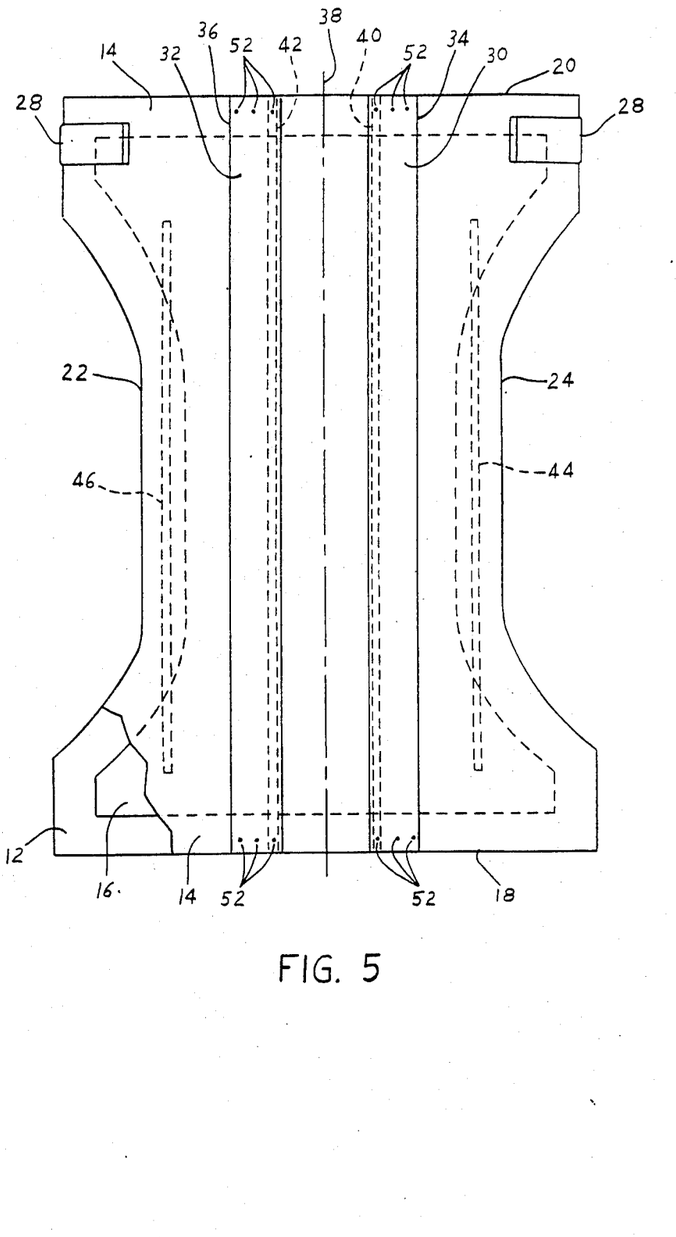
FIG. 5 is a plan view of a garment of the present invention showing full length flaps with an elastic member in each flap.

FIG. 5 is a plan view of a preferred embodiment of the present invention showing flaps 30, 32 with elastic members 40, 42 applied to flaps 30, 32 respectively. Indicated at 52 are bonds bonding respective ends of flaps 30, 32 to bodyside liner 14 at the front waist section 18 and back waist section 20. Any method of bonding may be used. A preferable method of bonding is autogenous bonding such as sonic bonding. Another method that is acceptable is adhesive bonding.

Figure 6:
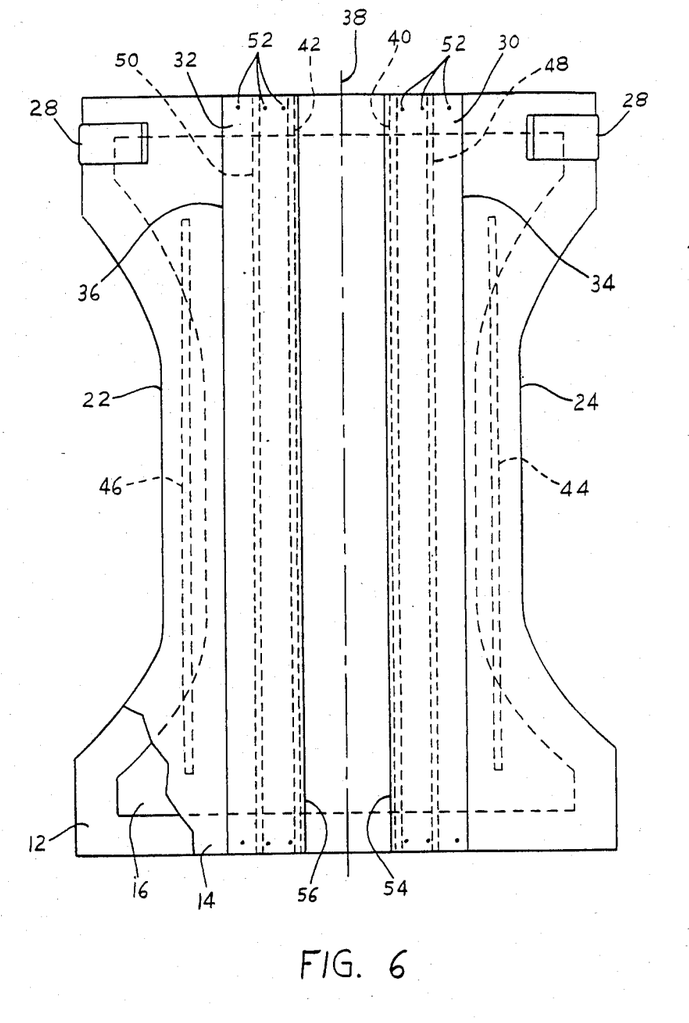
FIG. 6 is a plan view of a garment of the present invention showing full length flaps with two elastic members in each flap.

FIG. 6 is a plan view of an alternative embodiment of the present invention showing flaps 30, 32 having more width and having at least second elastic members 48, 50 applied to flaps 30, 32 respectively. The second elastic members are applied intermediate to lines 34, 36 and inwardly directed edges 54, 56 of flaps 30, 32. Again it should be noted that the width of flaps 30, 32 can vary and the illustrations and descriptions herein are for illustrative purposes only.

Figure 7:
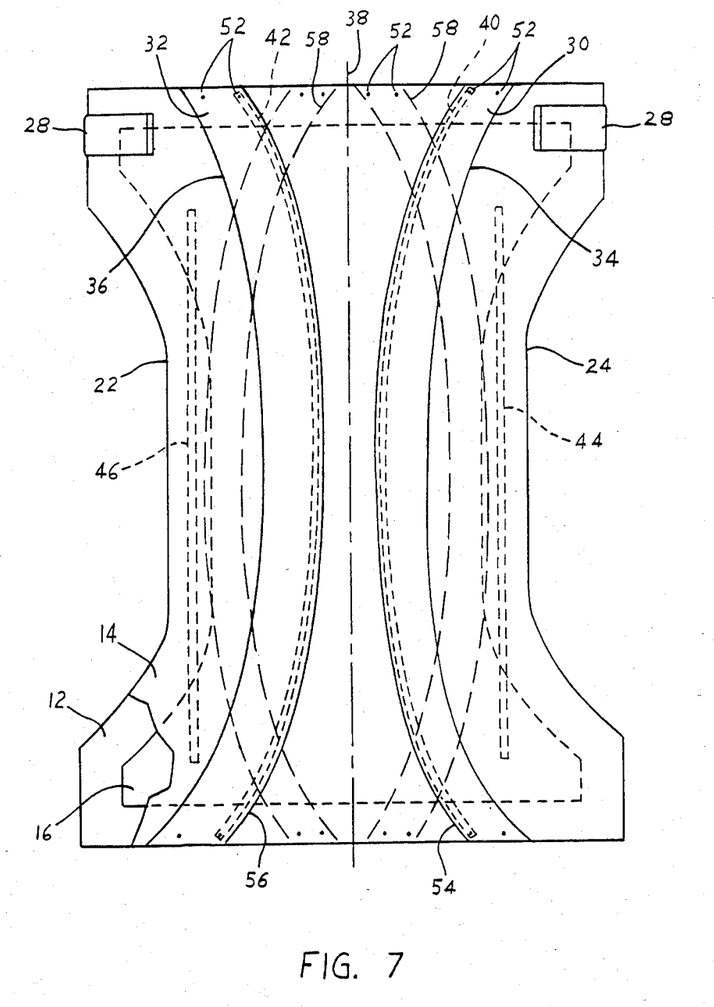
FIG. 7 is a plan view of a garment of the present invention showing full length curved flaps.

FIG. 7 is a plan view of further alternative embodiments of the garment of the present invention. Illustrated therein are flaps 30, 32 which are formed from or attached to inner liner 14 along lines 34, 36 respectively and lines 34, 36 are curved in relation to centerline 38. The lines 34, 36 may diverge from centerline 38 or the lines 34, 36 may converge toward the centerline 38 as shown by phantom line 58. As before flaps 30, 32 may be folded and bonded to inner liner 14 at respective ends of each flap. The flaps are folded and bonded whereby edges 54, 56 are directed toward centerline 38.

Figure 8:
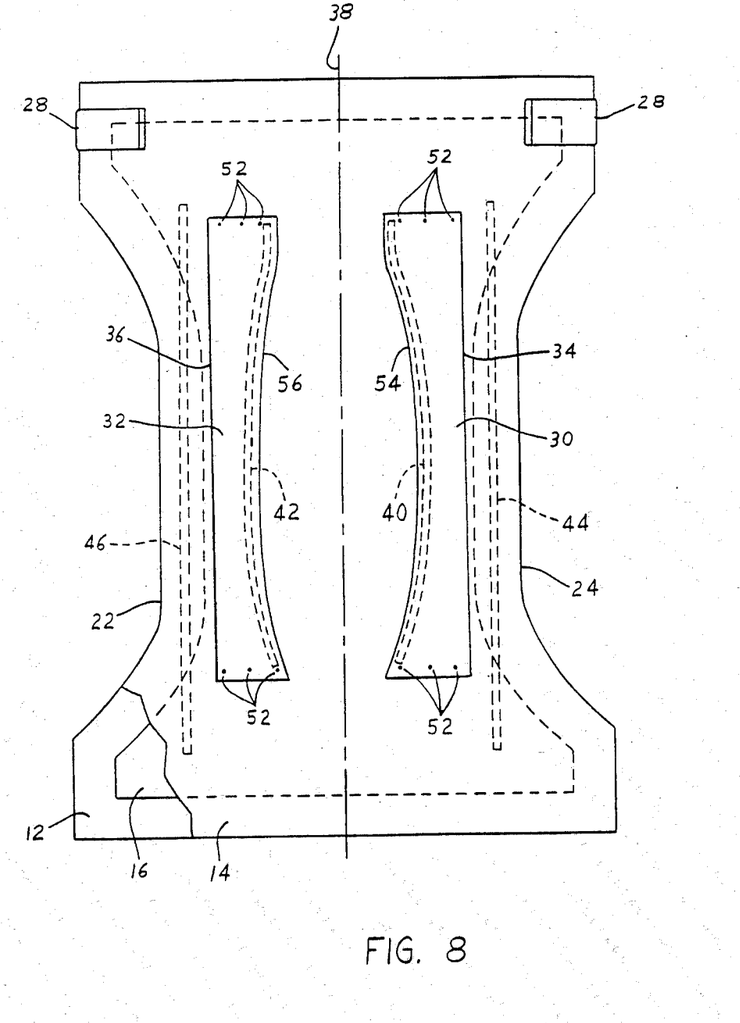
FIG. 8 is a plan view of a garment of the present invention showing partial flaps of varying width.

FIG. 8 is a plan view of still another alternative embodiment of the disposable garment of the present invention. This embodiment has flaps 30, 32 with varying width and with a length that extends from a first portion of the garment to a second portion of the garament where the total extent of the flaps is less than the full length of the garment. Typically, the flaps extend at least through the crotch section of the garment. Illustrated in FIG. 8 are flaps 30, 32, which have a width wider at respective ends of the flaps 30, 32 than at an intermediate portion of the flaps; however, it is comprehended within the scope of this invention that flaps 30, 32 may have a width wider at an intermediate portion of flaps than at respective ends. Also comprehended are combinations of the concepts described above wherein varying width flaps are attached to or formed from inner liner 14 along curved lines which converge to or diverge from centerline 38.

Thus, while the invention has now been described with reference to several preferred embodiments and illustrated with regard to a range of optional features, those skilled in the art will appreciate that various substitutions, omissions, modifications and changes may be made without departing from the spirit hereof. Accordingly, it is intended that the foregoing description be deemed merely exemplary of the preferred scope of the present invention and not to be deemed a limitation thereof.

I claim:

1. An absorbent garment comprising:
   a pair of waist sections together defining a waist opening;
   a crotch section disposed between said waist sections and a pair of elasticized leg openings separated by said crotch section;
   a back sheet;
   a liquid pervious bodyside liner attached to said backsheet;
   an absorbent body disposed between said liner and said backsheet; and
   first and second elasticized fluid pervious flaps, attached to or formed from said liner and spaced inwardly from said elasticized leg openings, respectively, defining a waste-containment pocket.

2. The garment of claim 1, wherein each of said first and second fluid pervious flaps comprises an essentially rectangular shape with first and second longitudinal sides and first and second base sides.

3. The garment of claim 2, wherein each of said first and second flaps is attached to or formed from said bodyside liner along respective first and second lines wherein said first and second lines are essentially parallel to a centerline of said garment wherein said centerline lies between said first and second sides.

4. The garment of claim 3, wherein each of said first and second longitudinal sides have a preselected length and each of said first and second base sides have a preselected width.

5. The garment of claim 4, wherein a first longitudinal side of each of said flaps is attached to said bodyside liner along respective said first and second lines.

6. The garment of claim 5, wherein said first longitudinal side of each of said flaps has a length sufficient to extend from said front waist section to said back waist section along said respective first and second lines.

7. The garment of claim 6, wherein said first longitudinal side of each of said flaps is sealed to said bodyside liner along respective said first and second lines.

8. The garment of claim 7, wherein said first and second base sides are attached to said bodyside liner wherein a second longitudinal side of each of said flaps is directed toward said centerline of said garment.

9. The garment of claim 8, wherein each of said elasticized flaps is elasticized at least one tensioned elastic member applied thereto.

10. The garment of claim 9, wherein said at least one elastic member is applied to each of said flaps with a first preselected tension.

11. The garment of claim 10, wherein said first preselected tension is sufficient to cause said second longitudinal side of each of said flaps to conform to a shape of a wearer.

12. The garment of claim 11, wherein each of said flaps has at least a second elastic member applied thereto.

13. The garment of claim 12, wherein said at least a second elastic member is applied intermediate said at least one elastic member and said first longitudinal side and wherein said at least a second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of wearer.

14. The garment of claim 13, wherein said preselected width of said first and second base sides is selected to be in the range of about one half inch to a width sufficient for said second longitudinal side to be essentially coterminous with said centerline.

15. The garment of claim 2, wherein each of said first and second flaps is attached to said bodyside liner along respective first and second lines wherein said first and second lines are curved and symmetrically oppositely disposed around a centerline of said garment wherein said centerline lies between said first and second sides.

16. The garment of claim 15, further comprising front and back waist sections and wherein said first and second lines are mutally divergent from said centerline in at least one of said front waist section or said back waist section.

17. The garment of claim 16, wherein said first and second lines are mutually divergent from said centerline in said back waist section.

18. The garment of claim 17, wherein each of said first and second longitudinal sides has a preselected length and said first and second base sides have a preselected width.

19. The garment of claim 18, wherein a first longitudinal side of each of said flaps is attached to said bodyside liner along respective ones of said first and second lines.

20. The garment of claim 19, wherein said first longitudinal side of each of said flaps has a length sufficient to extend from said front waist section to said back waist section along said first and second curved lines.

21. The garment of claim 20, wherein said first and second base sides are attached to said bodyside liner wherein a second longitudinal side of each of said flaps is directed toward said centerline of said garment.

22. The garment of claim 21, wherein each of said flaps has at least one elastic member applied thereto.

23. The garment of claim 22, wherein said at least one elastic member is applied essentially at said second longitudinal side.

24. The garment of claim 23, wherein said at least one elastic member is applied to each of said flaps with a first preselected tension.

25. The garment of claim 24, wherein said first preselected tension is sufficient to cause said second longitudinal side of each of said flaps to conform to a shape of a wearer.

26. The garment of claim 25, wherein each of said flaps has at least a second elastic member applied thereto.

27. The garment of claim 26, wherein said at least a second elastic member is applied intermediate said at least one elastic member and said first longitudinal side and wherein said at least second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

28. The garment of claim 27, wherein said preselected width of said first and second base sides of each of said flaps is selected to be in the range of about one half inch to a width sufficient for each of said second longitudinal sides of each of said flaps to be essentially coterminous with said centerline.

29. The garment of claim 5, wherein said first longitudinal side of each of said flaps has a length sufficient to extend from a first portion of said garment to a second portion of said garment.

30. The garment of claim 29, wherein said first longitudinal side of each of said flaps has a length sufficient to extend from a first portion of said garment to a second portion of said garment along respective said first and second lines which extend through said crotch section of said garment wherein said crotch section is intermediate said front waist section and said back waist section.

31. The garment of claim 30, wherein said first and second base sides of each of said flaps are attached to said bodyside liner whereby a second longitudinal side of each of said flaps is directed toward said centerline of said garment.

32. The garment of claim 31, wherein each of said flaps has at least one elastic member applied thereto.

33. The garment of claim 32, wherein said at least one elastic member is applied essentially at said second longitudinal side.

34. The garment of claim 33, wherein said at least one elastic member is applied to each of said flaps with a first preselected tension.

35. The garment of claim 34, wherein said first preselected tension is sufficient to cause said second longitudinal side of each of said flaps to conform to a shape of a wearer.

36. The garment of claim 35, wherein each of said flaps has at least a second elastic member applied thereto.

37. The garment of claim 36, wherein said at least a second elastic member is applied intermediate said at least one elastic member and said first longitudinal side and wherein said at least a second elastic member is applied with a second preselected tension wherein said second preselected tension can be greater than, less or equal to said first preselected tension and wherein said first and second preselected tensions are selected to cooperate to cause said second longitudinal side of each of said flaps to conform to a shape of a wearer.

38. The garment of claim 37, wherein said preselected width of said first and second base sides is selected to be in the range of about one half inch to a width sufficient for said second longitudinal side to be essentially coterminous with said centerline.

39. The garment of claim 18, wherein said first longitudinal side of each of said flaps has a length sufficient to extend from a first portion of said garment to a second portion of said garment.

40. The garment of claim 39, wherein said first longitudinal side of each of said flaps has a length sufficient to extend from a first portion of said garment to a second portion of said garment along respective said first and second curved lines which extend through said crotch section of said garment wherein said crotch section is intermediate said front waist section and said back waist section.

41. The garment of claim 40, wherein said first and second base sides of each of said flaps are attached to said bodyside liner whereby a second longitudinal side of each of said flaps is directed toward said centerline of said garment.

42. The garment of claim 41, wherein each of said flaps has at least one elastic member applied thereto.

43. The garment of claim 42, wherein said at least one elastic member is applied essentially at said second longitudinal side.

44. The garment of claim 43, wherein said at least one elastic member is applied to each of said flaps with a first preselected tension.

45. The garment of claim 44, wherein said first preselected tension is sufficient to cause said second longitudinal side of each of said flaps to conform to a shape of a wearer.

46. The garment of claim 45, wherein each of said flaps has at least a second elastic member applied thereto.

47. The garment of claim 46, wherein said at least a second elastic member is applied intermediate said at least one elastic member and said first longitudinal side and wherein said at least a second elastic member is applied with a second preselected tension wherein said second preselected tension can be greater than, less than or equal to said first preselected tension and wherein said first and second preselected tensions are selected to cooperate to cause said second longitudinal side of each of said flaps to conform to a shape of a wearer.

48. The garment of claim 47, wherein said preselected width of said first and second base sides of each of said flaps is selected to be in the range of about one half inch to a width sufficient for each of said second longitudinal sides of each of said flaps to be essentially coterminous with said centerline.

49. An absorbent garment comprising:
a pair of waist sections together defining a waist opening;
a crotch section disposed between said waist sections and a pair of elasticized leg openings separated by said crotch section;
a backsheet;
a liquid pervious bodyside liner attached to said backsheet;
an absorbent body disposed between said liner and said backsheet; and
first and second elasticized fluid pervious flaps each having a longitudinal side, a first and second base side and a fourth side wherein a distance between said longitudinal side and said fourth side comprises a width of said flaps and wherein said width varies between said first and second base side and wherein said longitudinal side is attached or formed from said bodyside liner and spaced inwardly of said elasticized leg openings, respectively, defining a waste containment pocket.

50. The garment of claim 49, wherein each of said first and second flaps is attached to or formed from said bodyside liner along respective first and second lines which are symmetrically disposed on a first and second side of a centerline of said garment wherein said centerline lies between said first and second sides.

51. The garment of claim 50, wherein said flaps have a preselected length.

52. The garment of claim 51, wherein said preselected length is sufficient to extend from a first portion of said garment to a second portion of said garment.

53. The garment of claim 52, wherein said preselected length is sufficient to extend from said front waist section to said back waist section along said first and second lines.

54. The garment of claim 53, wherein each of said flaps has at least one elastic member applied thereto.

55. The garment of claim 54, wherein said at least one elastic member is applied essentially at said fourth side of each of said flaps.

56. The garment of claim 55, wherein said at least one elastic member is applied to each of said flaps with a first preselected tension.

57. The garment of claim 56, wherein said first preselected tension is sufficient to cause said fourth side of each of said flaps to conform to a shape of a wearer.

58. The garment of claim 57, wherein each of said flaps has at least a second elastic member applied thereto.

59. The garment of claim 58, wherein said at least a second elastic member is applied intermediate said at least one elastic member and said longitudinal side and wherein said at least a second elastic member is applied with a second preselected tension wherein said second preselected tension can be greater than, less than or equal to said first preselected tension and wherein said first and second preselected tensions are selected to cooperate to cause said fourth side of each flaps to conform to a shape of a wearer.

60. An absorbent garment comprising:
a pair of waist sections together defining a waist opening;
a crotch section disposed between said waist sections and a pair of elasticized leg openings separated by said crotch section;
a backsheet;
a liquid pervious bodyside liner attached to said backsheet;
an absorbent body disposed between said liner and said backsheet; and
first and second elasticized liquid pervious flaps, formed from said bodyside liner and spaced inwardly of said elasticized leg openings, respectively, defining a waste containment pocket.

61. The garment of claim 60, wherein each of said first and second flaps is formed along respective first and second lines which are symmetrically disposed on a first and second side of a centerline of said garment wherein said centerline lies between said first and second sides.

62. The garment of claim 61, wherein each of said flaps extends from said front waist section to said back waist section along said first and second lines.

63. The garment of claim 62, wherein each end of said flaps is attached to said bodyside liner whereby said flaps are directed toward said centerline of said garment.

64. The garment of claim 63, wherein each of said flaps is elasticized by at least one tensioned elastic member applied thereto.

65. The garment of claim 64, wherein said elastic member is applied with a preselected tension sufficient to cause said flap to conform the shape of a wearer.

66. The garment of claim 65, wherein each of said flaps has at least a second elastic member applied thereto.

67. The garment of claim 66, wherein said second elastic member is applied with a tension selected to cooperate with said preselected tension of said at least one elastic member to cause each of said flaps to conform to a shape of a wearer of said garment.

* * * * *

UNITED STATES PATENT AND TRADEMARK OFFICE
CERTIFICATE OF CORRECTION

PATENT NO. : 4,704,116

DATED : November 3, 1987

INVENTOR(S) : Kenneth M. Enloe

It is certified that error appears in the above-identified patent and that said Letters Patent is hereby corrected as shown below:

Claims 1, 16, 19, 30, 40, 49 and 60 should be deleted to appear as shown on the attached sheets.

1.  An absorbent garment comprising:

a back sheet;

a liquid pervious bodyside liner, essentially coterminous with said back sheet, defining front and back waist sections and opposed first and second sides connecting said waist section, including a pair of leg sections delimited along said sides, each of said leg sections having a tensioned elastic member disposed therealong, forming elasticized leg gathers;

an absorbent body disposed between said liner and back sheet; and first and second elasticized fluid pervious flaps, attached to or formed from said bodyside liner and spaced inwardly of said leg elastic members, respectively, defining a waste containment pocket.

16.  The garment of claim 15, wherein said first and second lines are mutually divergent from said centerline in at least one of said front waist section or said back waist section.

19.  The garment of claim 18, wherein a first longitudinal side of each of said flaps is attached to said bodyside liner along respective said first and second lines.

UNITED STATES PATENT AND TRADEMARK OFFICE
CERTIFICATE OF CORRECTION

PATENT NO. : 4,704,116

DATED : November 3, 1987

INVENTOR(S) : Kenneth M. Enloe

Page 2 of 4

It is certified that error appears in the above-identified patent and that said Letters Patent is hereby corrected as shown below:

30. The garment of claim 29, wherein said first longitudinal side of each of said flaps has a length sufficient to extend from a first portion of said garment to a second portion of said garment along respective said first and second lines which extend through a crotch section of said garment wherein said crotch section is intermediate said front waist section and said back waist section.

40. The garment of claim 39, wherein said first longitudinal side of each of said flaps has a length sufficient to extend from a first portion of said garment to a second portion of said garment along respective said first and second curved lines which extend through a crotch section of said garment wherein said crotch section is intermediate said front waist section and said back waist section.

49. A garment comprising:

a back sheet;

a bodyside liner, essentially coterminous with said back sheet, defining front and back waist sections and opposed first and second sides connecting said waist sections, including a pair of leg sections delimited along said first and second sides, each of said leg sections having a tensioned elastic member disposed therealong, forming elasticized leg gathers; an absorbent body disposed between said liner and backsheet; and first and second elasticized fluid pervious flaps each having

UNITED STATES PATENT AND TRADEMARK OFFICE
CERTIFICATE OF CORRECTION

PATENT NO. : 4,704,116

DATED : November 3, 1987

INVENTOR(S) : Kenneth M. Enloe

It is certified that error appears in the above-identified patent and that said Letters Patent is hereby corrected as shown below:

a longitudinal side, a first and second base side and a fourth side wherein a distance between said longitudinal side and said fourth side comprises a width of said flaps and wherein said width varies between said first and second base side and wherein said longitudinal side is attached to or formed from said bodyside liner and spaced inwardly of said leg elastic members, respectively, defining a waste containment pocket.

60. A garment comprising:

a back sheet;

a liquid pervious bodyside liner, essentially coterminous with said back sheet, defining front and back waist sections and first and second sides connecting said waist sections, including a pair of leg sections delimited along said first and second sides, each of said leg section having a tensioned elastic member disposed therealong, forming elasticized leg gathers; an absorbent body disposed between said liner and backsheet; and

UNITED STATES PATENT AND TRADEMARK OFFICE
CERTIFICATE OF CORRECTION

PATENT NO.   :   4,704,116

DATED        :   November 3, 1987

INVENTOR(S)  :   Kenneth M. Enloe

It is certified that error appears in the above-identified patent and that said Letters Patent is hereby corrected as shown below:

first and second elasticized liquid pervious flaps, formed from said bodyside liner and spaced inwardly of said leg elastic members, respectively, defining a waste containment pocket.

Signed and Sealed this

Twelfth Day of April, 1988

*Attest:*

DONALD J. QUIGG

*Attesting Officer*       *Commissioner of Patents and Trademarks*

UNITED STATES PATENT AND TRADEMARK OFFICE
CERTIFICATE OF CORRECTION

PATENT NO. : 4,704,116
DATED : November 3, 1987
INVENTOR(S) : Kenneth M. Enloe

It is certified that error appears in the above-identified patent and that said Letters Patent is hereby corrected as shown below:

Column 2, line 5, delete "t" and substitute therefor --to--.

Column 6, line 3, delete "garament" and substitute therefor --garment--.

Claim 9, column 7, line 4, add the word "by" before the word "at".

In the previous Certificate of Correction in Claim 1, fifth line of the claim, delete the fifth word "section" and substitute therefor "sections".

Signed and Sealed this

Twenty-seventh Day of February, 1990

*Attest:*

JEFFREY M. SAMUELS

*Attesting Officer*     *Acting Commissioner of Patents and Trademarks*

US004704116B1

REEXAMINATION CERTIFICATE (4170th)

United States Patent [19]
Enloe

[11] B1 4,704,116
[45] Certificate Issued Oct. 17, 2000

[54] DIAPERS WITH ELASTICIZED SIDE POCKETS

[75] Inventor: Kenneth M. Enloe, Neenah, Wis.

[73] Assignee: Kimberly-Clark Corporation, Neenah, Wis.

Reexamination Request:
No. 90/005,479, Sep. 8, 1999

Reexamination Certificate for:
Patent No.: 4,704,116
Issued: Nov. 3, 1987
Appl. No.: 06/786,891
Filed: Oct. 11, 1985

Certificate of Correction issued Apr. 12, 1988.

Certificate of Correction issued Feb. 27, 1990.

Related U.S. Application Data

[63] Continuation-in-part of application No. 06/627,164, Jul. 2, 1984, abandoned.

[51] Int. Cl.[7] .............................. A61F 13/15; A61F 13/20
[52] U.S. Cl. ................ 604/385.27; 604/385.28; 604/358; 604/390
[58] Field of Search ...................... 604/385.2, 378, 604/390, 358

[56] References Cited

U.S. PATENT DOCUMENTS

| | | | |
|---|---|---|---|
| 3,561,446 | 2/1971 | Jones, Sr. ............................. | 604/385.1 |
| 3,759,261 | 9/1973 | Wang ..................................... | 604/361 |
| 3,860,003 | 1/1975 | Buell ..................................... | 128/287 |
| 3,885,568 | 5/1975 | Schaar ................................... | 604/385.1 |
| 3,886,941 | 6/1975 | Duane et al. ......................... | 604/385.1 |
| 4,041,951 | 8/1977 | Sanford ................................... | 604/375 |
| 4,333,782 | 6/1982 | Pieniak ................................. | 604/385.2 |
| 4,337,771 | 7/1982 | Pieniak et al. ...................... | 604/385.2 |
| 4,352,355 | 10/1982 | Mesek et al. ........................ | 604/385.2 |
| 4,381,782 | 5/1983 | Mazurak et al. ..................... | 604/385.2 |
| 4,402,688 | 9/1983 | Julemont .............................. | 604/385.2 |
| 4,490,148 | 12/1984 | Beckeström ........................... | 604/385 |
| 4,527,989 | 7/1985 | Karami . | |
| 4,695,278 | 9/1987 | Lawson ............................... | 604/385 A |
| 4,704,116 | 11/1987 | Enloe .................................. | 604/385 A |

FOREIGN PATENT DOCUMENTS

| | | |
|---|---|---|
| 39-33810 | 11/1964 | Japan . |
| 41-18359 | 8/1966 | Japan . |

OTHER PUBLICATIONS

Translation of JP 41–18359 Oct. 13, 1964 Tetsujiro Shikinami.
Patent Interference No. 102,274.

*Primary Examiner*—Mark O. Polutta

[57] ABSTRACT

A garment with a backsheet (12), a bodyside liner (14) essentially coterminous with the backsheet (12) and forming a shape with a front waist section (18), a back waist section (20) and side sections connecting the front waist section (18) to the back waist section (20) and first and second flaps (30, 32) formed from or attached to bodyside liner (14). Flaps (30, 32) may have elastic members (40, 42) applied thereto respectively. Flaps (30, 32) may be folded inwardly and respective ends thereof may be bonded to bodyside liner (14) so that edges of flaps are directed toward a centerline (38) of the garment. The flaps (30, 32) may be attached to or formed from bodyside liner (14) along lines (34, 36) which are parallel to centerline (38) or which diverge from or converge toward centerline (38). Additionally, flaps (30, 38) may have varying width and be less than full length.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–67 is confirmed.

* * * * *